United States Patent
Lin (10) Patent No.: US 6,745,898 B2
(45) Date of Patent: Jun. 8, 2004

(54) NEEDLE EXTRACTING AND RECOVERING DEVICE

(75) Inventor: Bih-Chern Lin, Taichung (TW)

(73) Assignee: Future Top Medical Environment Technic Co., Ltd., Taipei (TW)

( * ) Notice: Subject to any disclaimer, the term of this patent is extended or adjusted under 35 U.S.C. 154(b) by 58 days.

(21) Appl. No.: 10/145,201

(22) Filed: May 15, 2002

(65) Prior Publication Data

US 2003/0213713 A1 Nov. 20, 2003

(51) Int. Cl.⁷ .............................................. B65D 85/24
(52) U.S. Cl. ...................................... 206/366; 604/110
(58) Field of Search ................................ 206/363–369; 604/110, 192; 220/908, 910

(56) References Cited

U.S. PATENT DOCUMENTS

| | | | | |
|---|---|---|---|---|
| 4,807,344 A | * | 2/1989 | Kelson et al. .............. | 206/366 |
| 4,892,191 A | * | 1/1990 | Nakamura ................... | 206/366 |
| 4,986,811 A | * | 1/1991 | Thead et al. ................. | 604/110 |
| 5,417,659 A | * | 5/1995 | Gaba ........................... | 604/110 |
| 5,469,964 A | * | 11/1995 | Bailey ......................... | 206/364 |
| 5,791,471 A | * | 8/1998 | Radmand .................... | 206/366 |
| 6,382,417 B2 | * | 5/2002 | Kanner et al. .............. | 206/366 |

\* cited by examiner

*Primary Examiner*—Luan K. Bui
(74) *Attorney, Agent, or Firm*—Troxell Law Office PLLC (57) ABSTRACT

A needle extracting and recovering device, the device is provided on the top of a case thereof with a needle insertion hole for insertion of a needle holder of a syringe with a needle to be extracted, an inclined rotation axle mechanism including a rotating knob is provided below the needle insertion hole, the rotation axle mechanism is provided on one lateral side thereof with a slit for inserting of the needle, the needle is extracted from the needle holder by rotating the rotating knob to rotate the rotation axle mechanism.

6 Claims, 7 Drawing Sheets

NEEDLE EXTRACTING AND RECOVERING DEVICE

BACKGROUND OF THE INVENTION

1. Field of the Invention

The present invention is related to a needle extracting and recovering device; and especially to a device able to separate a needle from a needle holder to effectively recover metal resource, the device is suitable to be a needle extractor used in various medical spots.

2. Description of the Prior Art

A medical syringe is mainly comprised of a cylindrical syringe body, a needle and a needle holder. A needle fixing seat used presently is generally made of plastic, one end of which is fitted over the opening end of the cylindrical syringe body, and the other end is fitted in the needle.

Earlier medical syringes were mostly recovered for repeated use; while the syringes used in public and private hospitals in the present time are not recovered, they are discarded after use. However, such a principle of discarding has created a problem of unknowing how to deal with the discarded needles although it can avoid the problem of infection by repeated use of needles, thus a quite large trouble is formed in environmental conservation.

To solve the above stated problems, there has been some needle extractor to extract a needle being inserted between two pressing rollers by rotating the rollers. Such a structure can have the needle removed from the cylindrical syringe body, however, sufficient twisting force of a motor is required to remove the needle, thereby considerable electric power is consumed, and cost is increased, damage ratio of the electric machine is overly high. The motive of the present invention is to provide a needle extracting device able to easily extract and recover needles without consumption of electric power and to get rid of the defects resided in the conventional needle extractor.

SUMMARY OF THE INVENTION

The primary object of the present invention is to provide a needle extracting and recovering device able to easily extract needles from a needle holder.

The secondary object of the present invention is to provide a needle extracting and recovering device without consumption of electric power to thereby lower cost.

Another object of the present invention is to provide a needle extracting and recovering device suitable for cylindrical syringe bodies of various sizes.

A further object of the present invention is to provide a needle extracting and recovering device able to scrap off the cured glue on the connecting end of the needle.

To get the above object, the present invention is provided on the top of the housing thereof with a needle insertion hole for insertion of a needle holder with its needle to be extracted. An inclined rotation axle mechanism including a rotating knob is provided below the needle insertion hole, the rotation axle mechanism is provided on one lateral side thereof with a slit, a knife is provided at a suitable location above the slit, in order that the metal needle is positioned here to be extracted from the needle holder by rotating the knob to rotate the rotation axle mechanism; meantime, the knife can clearly scrape off the cured glue on the needle.

The present invention will be apparent in its features and structure after reading the detailed description of the preferred embodiment thereof in reference to the accompanying drawings.

DETAILED DESCRIPTION OF THE PREFERRED EMBODIMENT

Figure 1:
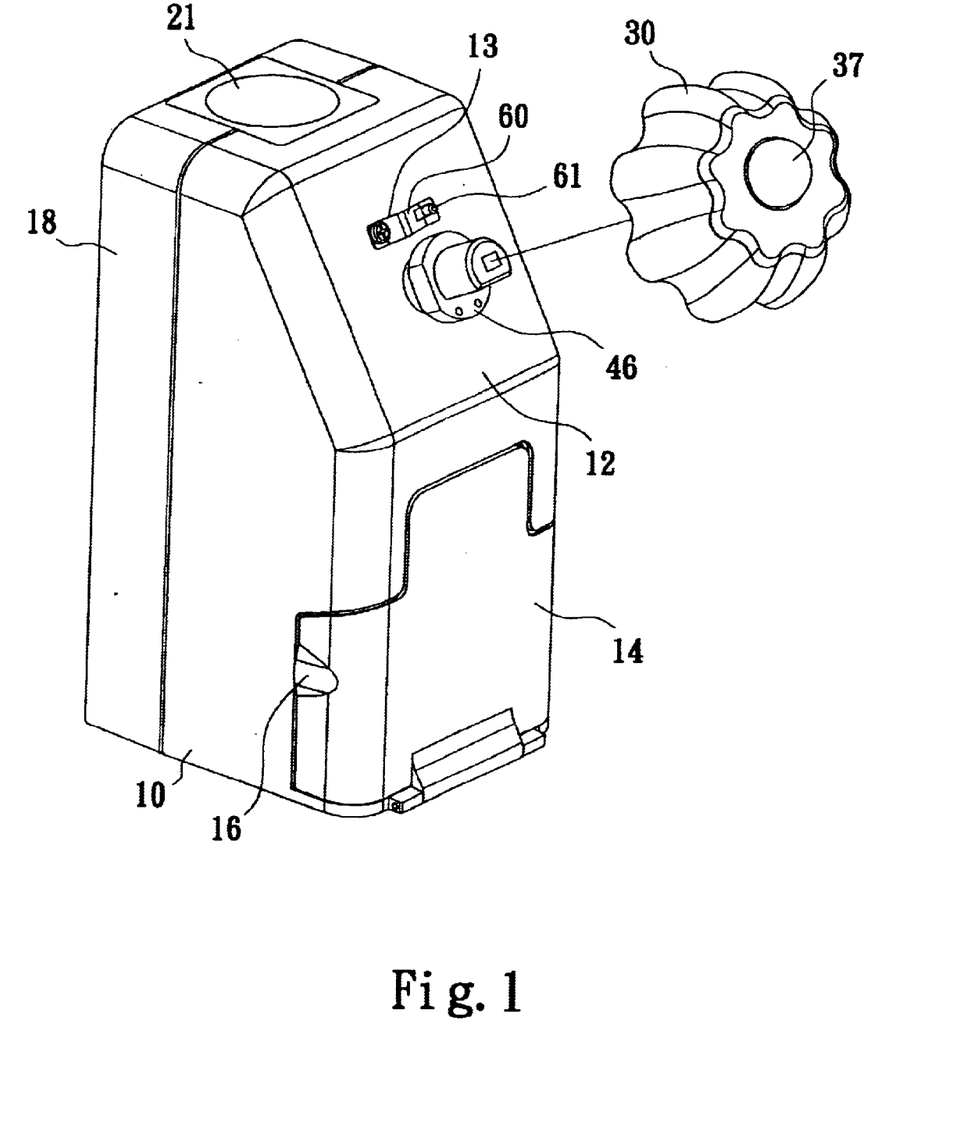
FIG. 1 is a perspective view of a preferred embodiment of the present invention.
Figure 2:
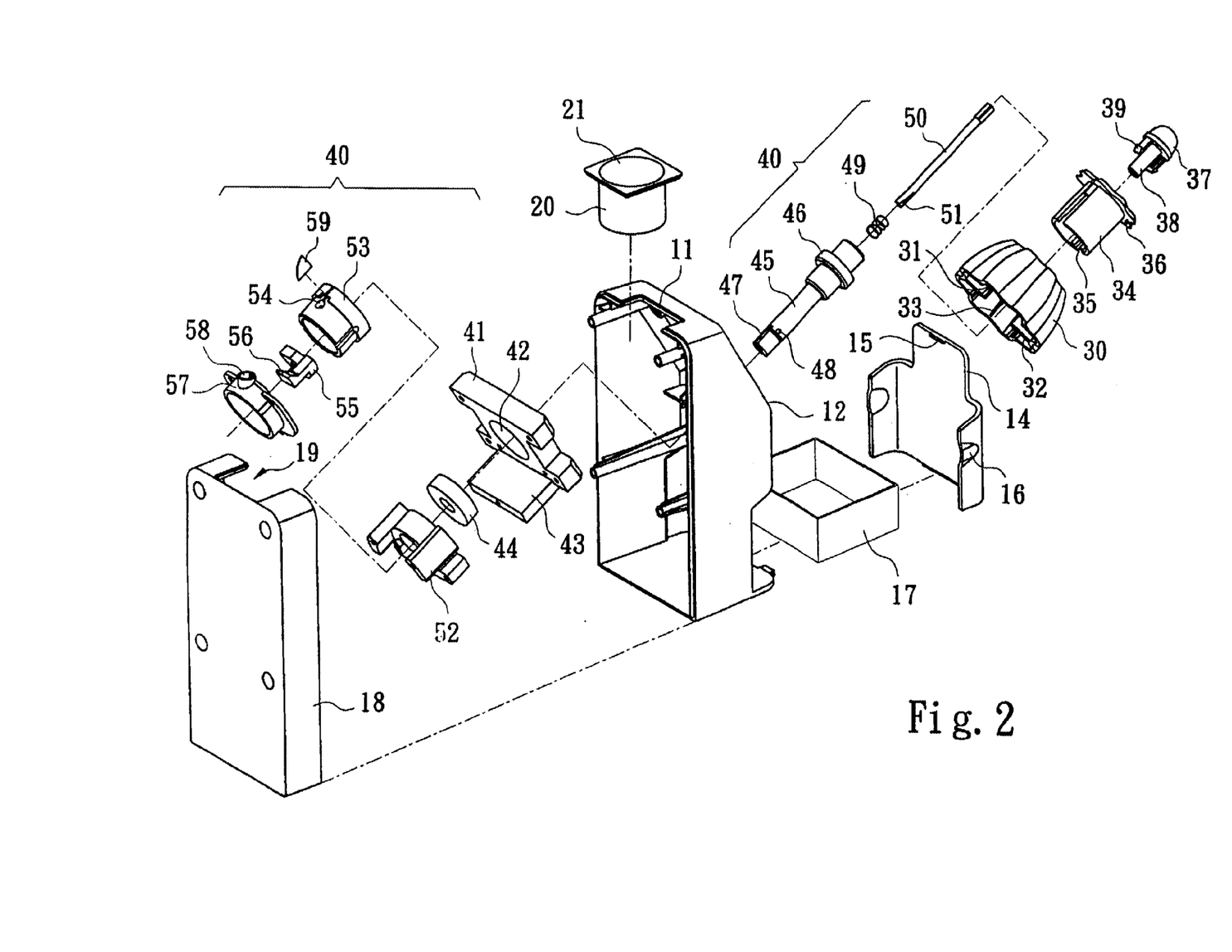
FIG. 2 is an analytic perspective view showing the elements composing the embodiment of the present invention.
Figure 3:
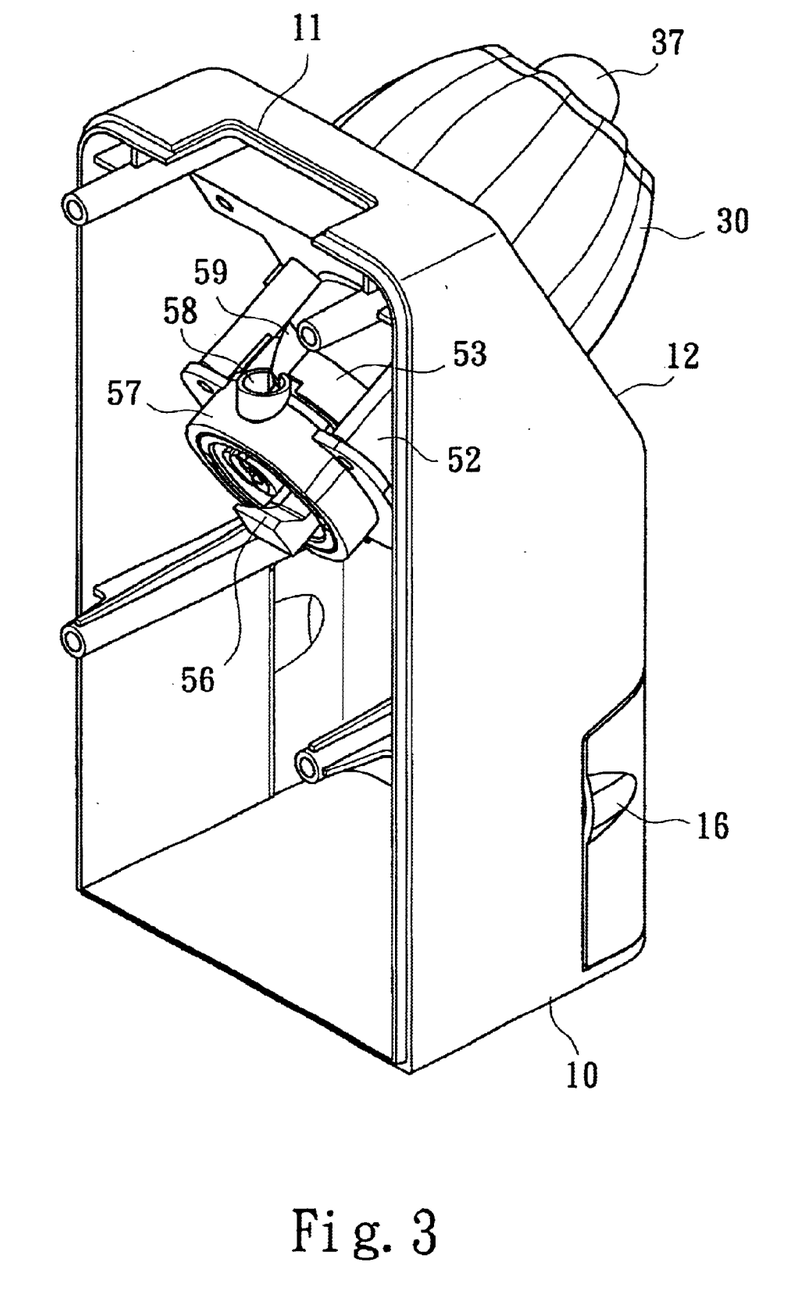
FIG. 3 is a perspective view showing the embodiment of the present invention after assembling of the elements of FIG. 2.

Referring to FIGS. 1–3, the present invention includes a case of suitable size, the case is comprised of a front half housing 10 and a rear half housing 18 connecting with each other in a confronting mode, and is provided on the top thereof with a needle insertion hole 21, a rotating knob 30 is provided on the upper portion of the case, and an openable cover 14 is provided on the lower portion of the case.

Wherein, the front half housing 10 is made by injection molding of plastic, and is provided internally thereof at suitable locations with threaded stubs, the top thereof is provided with a slot 11, and the front half housing 10 is provided on the upper portion thereof with an inclined surface 12 which has an axle hole at the center thereof. A positioning protruding block 13 is provided at a suitable location on the axle hole, one side of the protruding block 13 is provided with an engaging hole 61, while the other side is provided with a threaded hole to lock by means of the screw thread to a spring leaf 60 having a protruding portion at the center thereof. The front half housing 10 is provided on the lower portion thereof with an opening with a large area to connect with the cover 14 having a contour coincident therewith; the cover 14 is provided on the top thereof with an engaging member 15, and is provided on the two lateral sides thereof each with a finger holding area 16; the case is provided further with a collecting box 17 therein to be taken in or out when the cover 14 is opened.

The rear half housing 18 is provided in cooperation with the front half housing 10, it is provided on the top thereof with a slot 19 too, the slot 19 corresponds with the above-mentioned slot 11, so that the top surface of the case can have a rectangular hole for receiving a cylinder 20 forming the needle insertion hole 21 and with a rectangular frame.

The rotating knob 30 is provided centrally thereof with a hole of which the inner wall is provided with two protruding members 31, the rotating knob 30 has two connecting walls in connecting with the hole and in a mutually orthogonal state, one of the two connecting walls is in the same plane as that of the rotating knob 30 and is used as a larger reference member 32; while the other connecting wall is depressed and not in the same plane as that of the rotating knob 30 and is used as a smaller reference member 33. The hole with the protruding members 31 is engaged with an inner cylinder 34 with two slits 35 corresponding in position to the protruding members 31. The inner cylinder 34 is provided on the top thereof with a down protruding positioning stub 36; the inner cylinder 34 is thereby firmly connected in the rotating knob 30 by providing the protruding positioning stub 36 and the two slits 35. The inner cylinder 34 is mounted therein with a cover 37 with a central bottom hollow abutting rod 38 and two lateral engaging hooks 39.

A rotation axle mechanism 40 which is comprised of a fixing seat 41, a plurality of members and a rotation axle 45 connecting by screw threads; wherein, the fixing seat 41 is provided peripherally thereof with screw holes, a pending sheet 43 is extended from the bottom thereof, the pending sheet 43 is provided in the middle thereof with a screw hole. The fixing seat 41 is provided centrally thereof with a stepped hole 42 for receiving a bearing 44 which in sequence is connected with a positioning block 52, a collar 53, a stop block 55 and an enveloping ring 57. The positioning block 52 is provided laterally thereof with two threaded columns; the collar 53 is provided peripherally thereof with a hole 54 and a slit and is connected between the two threaded columns of the positioning block 52. The stop block 55 is provided with a protrusion 56 and is screw connected to the bottom of the collar 53. Finally, the enveloping ring 57 is fitted over the collar 53, to render a needle hole stub 58 with a slit on the enveloping ring 57 to align with the hole 54 of the collar 53; then the enveloping ring 57 is screw connected respectively to the positioning block 52 and the pending sheet 43 of the fixing seat 41. Moreover, a knife 59 is provided in a slit on the collar 53 and in the needle hole stub 58 with a slit too. The rotation axle 45 has a central hole of which the inner wall has a stepped portion in order to receive therein a spring 49 and a thinner axle 50, and is provided on the upper area thereof with an annulus 46, on the bottom thereof with a slit 47; the slit 47 is provided on the upper end thereof with a hole 48. When the rotation axle 45 is extended through the axle hole on the upper inclined surface 12 of the front half housing 10 to abut the annulus 46 of the rotation axle 45 against the axle hole, the slit 47 on the bottom thereof is exactly placed in the collar 53 to be under the hole 54 of the collar 53 and the needle hole stub 58 of the enveloping ring 57, while the top end thereof is extended into the inner cylinder 34 of the rotating knob 30; the top end of the thinner axle 50 in the rotation axle 45 is tightly abutted on the inner wall of the bottom hollow abutting rod 38 of the cover 37, the cover 37 is abutted on the inner wall of the inner cylinder 34 by means of the two lateral engaging hooks 39 to thereby complete the rotation axle mechanism 40 and to complete assembling of the present invention.

Figure 4:
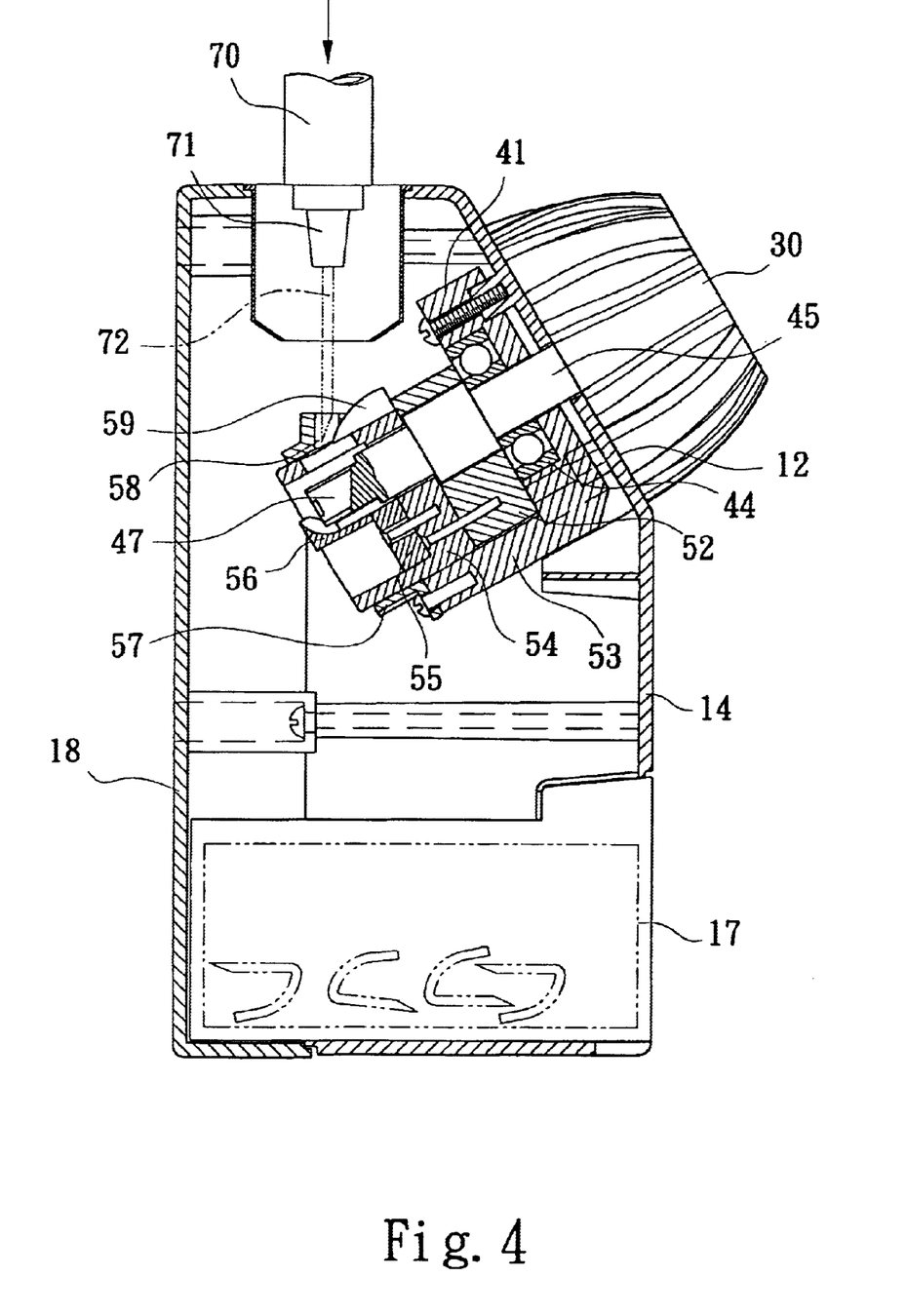
FIG. 4 is a schematic sectional view showing use of the present invention.

Referring to FIG. 4, the larger reference member 32 of the rotating knob 30 is rotated to an upper position in the first place (it is alright by rotating clockwise or counterclockwise, by the fact that the spring leaf 60 has a protruding portion at the center thereof, no matter the larger reference member 32 or the smaller reference member 33 passes over the spring leaf 60, it can be known from the amount of force exerted), the slit 47 of the rotation axle 45 is arranged exactly under the needle insertion hole 21; a metal needle 72 of a discarded syringe 70 is inserted into the case through the needle insertion hole 21, the metal needle 72 is extended through the needle hole stub 58 of the enveloping ring 57 and the hole 54 of the collar 53 into the slit 47 of the rotation axle 45 and is abutted against the protrusion 56 of the stop block 55. Now, the rotation axle 45 is rotated together with the rotating knob 30, thereby the metal needle 72 in the slit 47 on the front end of the rotation axle 45 is bent and wrapped onto the rotation axle 45 to be separated from a needle holder 71; the cured glue on the connecting end of the needle 72 with the needle holder 71 can be clearly scraped off by the knife 59 when the needle 72 is separated from the needle holder 71, while the extracted needle 72 drops into the collecting box 17 (as shown in FIGS. 5a–5c) for subsequent concentrated processing.

Figure 5A:
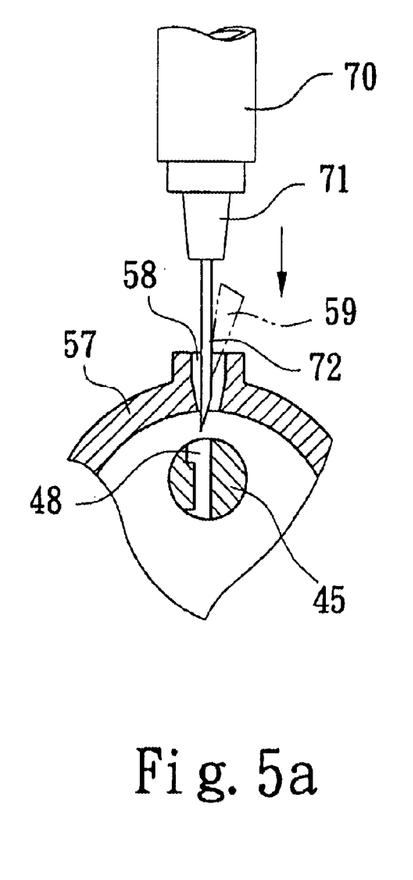
FIGS. 5a–5c are schematic views showing extracting the needle in the present invention.
Figure 5B:
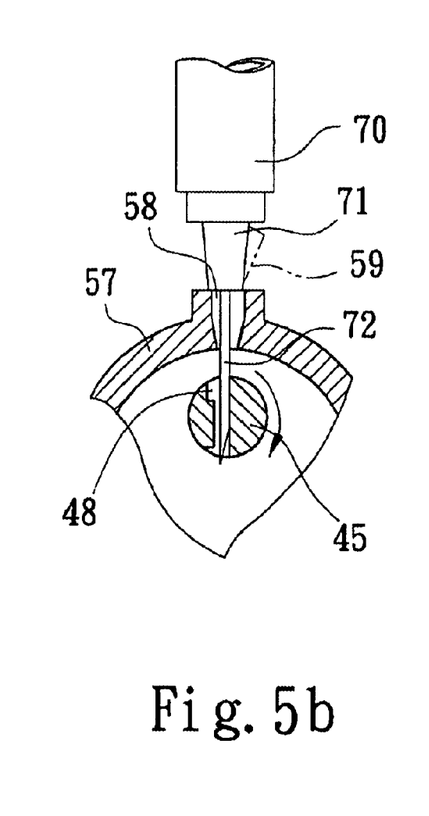
Figure 5C:
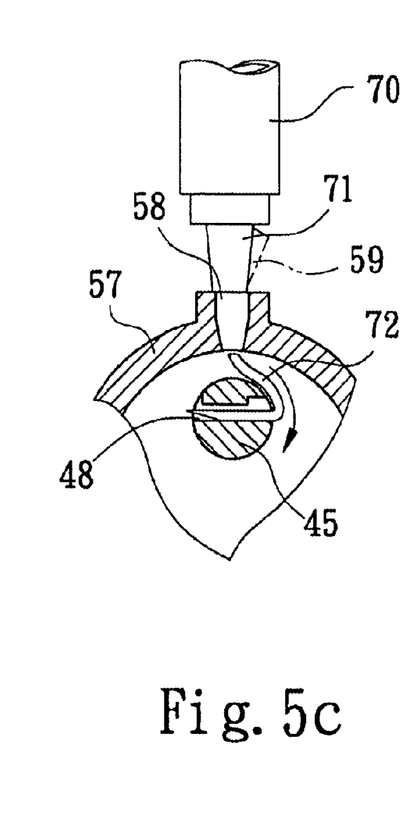
Figure 6:
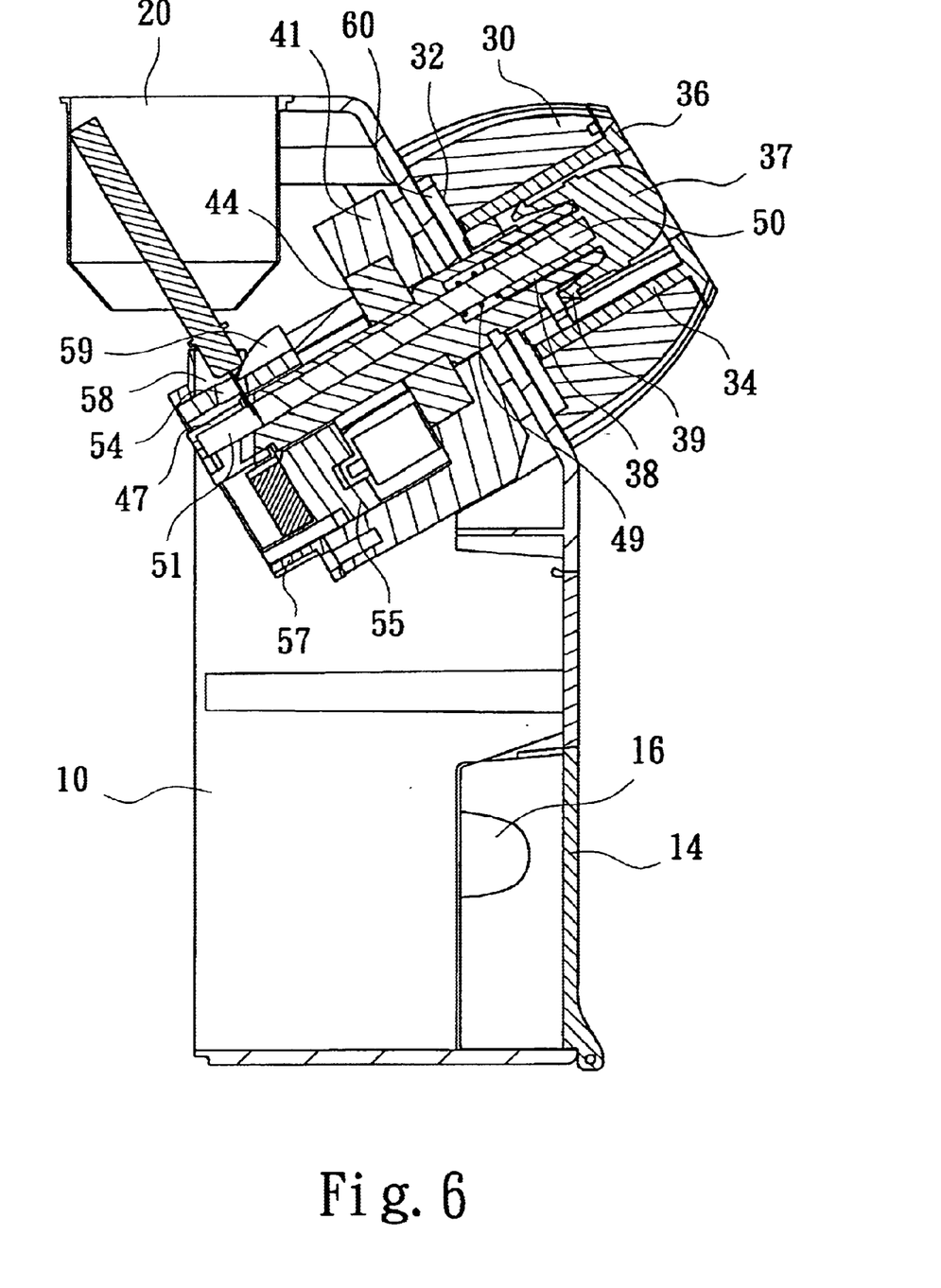
FIG. 6 is a sectional view showing another preferred embodiment of the present invention.

Referring now to FIG. 6, if the discarded syringe 70 is a thinner one, firstly, the smaller reference member 33 of the rotating knob 30 is rotated to an upper position, the metal needle 72 of the thinner syringe 70 is placed in the needle insertion hole 21, the metal needle 72 is extended through the hole 48 perpendicular to the slit 47 on the end of the rotation axle 45, then the cover 37 is pressed down to render a "V" shaped groove 51 on the end of the thinner axle 50 to extend into the slit 47 of the rotation axle 45, thereby the metal needle 72 is clamped in the "V" shaped groove 51; the rotating knob 30 is rotated now in the similar way as stated before, the metal needle 72 is bent and wrapped onto the thinner axle 50 to be separated; the cured glue can be scraped off by the knife 59 when in separation, while the extracted needle 72 drops into the collecting box 17 (as shown in FIGS. 5a–5c) for subsequent concentrated processing.

Figure 7:
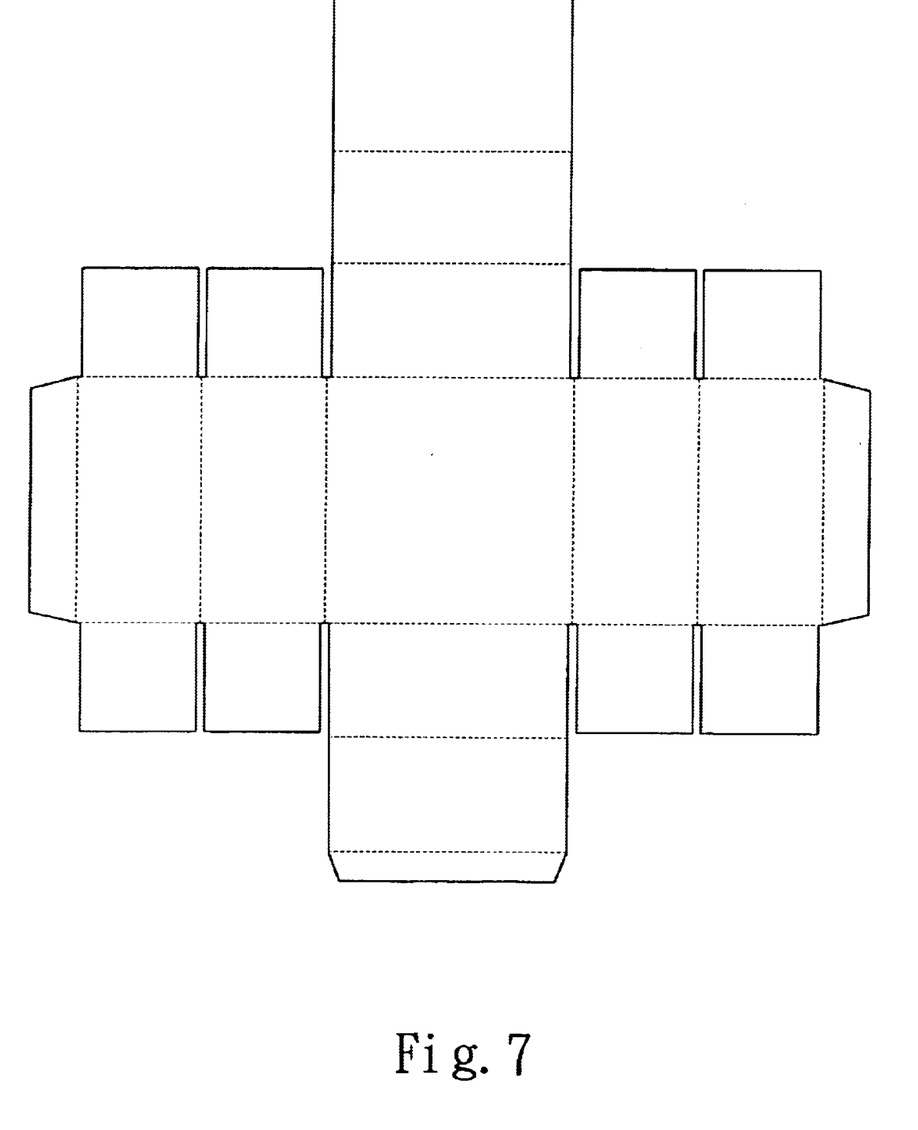
FIG. 7 is a schematic view showing an unfolded collecting box of the present invention.

And referring to FIG. 7 which shows the collecting box 17 in an unfolded state, the collecting box 17 is made from paper in two layers; when the collecting box 17 is fully filled with a lot of needles 72, it is taken out and is covered with a paper lid to protect a user from hurting by stabbing. The rotation axle mechanism of the present invention can change the orientation of a metal needle during rotation, and it is quite close to the area where the metal needle is stuck with the needle holder, hence the rotation axle mechanism can extract the metal needle without a too large force.

In conclusion, the needle extracting and recovering device of the present invention can extract a dangerous metal needle on the front end of a discarded syringe without consumption of electric power and energy source; thereby it can reduce the process and cost of recovery of discarded medical wastes; more importantly, it can effectively reduce the volume of the discarded medical wastes.

Having thus described my invention which is novel and industrially practical, what I claim as new and desire to be secured by Letters Patent of the United States are:

1. A needle extracting and recovering device, said device is provided on the top of a case thereof with a needle insertion hole for insertion of a needle holder of a syringe with a needle to be extracted, an inclined rotation axle mechanism including a rotating knob is provided below said needle insertion hole, said rotation axle mechanism is provided on one lateral side thereof with a slit for inserting of said needle, said needle is extracted from said needle holder by rotating said rotating knob to rotate said rotation axle mechanism, wherein, said case is comprised of a front half housing and a rear half housing connecting with each other in a confronting mode and has a slot on the top surface of said case after connecting, wherein said front half housing is provided on the upper portion thereof with an axle hole, a positioning protruding block is provided on said axle hole to lock and position a spring leaf having a protruding portion, said front half housing is provided on the lower portion thereof with an opening with a large area to connect with a cover having a contour coincident therewith, said cover is provided on the top thereof with an engaging member, and is provided on the two lateral sides thereof each with a finger holding area, a collecting box is placed in said case when said cover is opened.

2. The needle extracting and recovering device as claimed in claim 1, wherein said collecting box is made from paper in two layers, and is covered with a paper lid.

3. A needle extracting and recovering device, said device is provided on the top of a case thereof with a needle insertion hole for insertion of a needle holder of a syringe with a needle to be extracted, an inclined rotation axle mechanism including a rotating knob is provided below said needle insertion hole, said rotation axle mechanism is provided on one lateral side thereof with a slit for inserting of said needle, said needle is extracted from said needle holder by rotating said rotating knob to rotate said rotation axle mechanism, wherein, said rotating knob includes an inner cylinder and a cover, and is provided centrally thereof with a hole of which the inner wall is provided with two protruding members each having a positioning hole on the top thereof, and has two connecting walls in connecting with said hole and in a mutually orthogonal state, one of said two connecting walls is in the same plane as that of said rotating knob and is used as a larger reference member; while the other of said connecting walls is depressed and not in the same plane as that of said rotating knob and is used as a smaller reference member;

said inner cylinder is provided with two slits corresponding in position to said protruding members of said hole, and is provided on the top thereof with a down protruding positioning stub;

said cover is provided with a central bottom hollow abutting rod and two lateral engaging hooks.

4. The needle extracting and recovering device as claimed in claim 3, wherein a thinner axle is provided in said rotation axle and is tightly abutted on the inner wall of said bottom hollow abutting rod of said cover of said rotating knob.

5. A needle extracting and recovering device, said device is provided on the top of a case thereof with a needle insertion hole for insertion of a needle holder of a syringe with a needle to be extracted, an inclined rotation axle mechanism including a rotating knob is provided below said needle insertion hole, said rotation axle mechanism is provided on one lateral side thereof with a slit for inserting of said needle, said needle is extracted from said needle holder by rotating said rotating knob to rotate said rotation axle mechanism, wherein, said rotation axle mechanism is comprised of a fixing seat, a plurality of members and a rotation axle connecting by screw threads, including:

said fixing seat being provided peripherally thereof with screw holes for screw connecting to said case, and being provided centrally thereof with a stepped hole for receiving a bearing, a pending sheet is extended from the bottom of said fixing seat, said pending sheet is provided thereon with a screw hole;

said rotation axle having a central hole of which the inner wall has a stepped portion in order to receive therein a spring and a thinner axle, and being provided on the upper area thereof with an annulus, on the bottom thereof with a slit, said slit is provided on the upper end thereof with a hole;

a positioning block being adapted to screw connecting with said fixing seat, and being provided laterally thereof with two threaded columns;

a collar adapted to fitting over said annulus of said rotation axle being connected between said two threaded columns, the diameter of said collar is coincident with that of said positioning block, said collar is stepped on the surface thereof and is provided peripherally thereof with a hole and a slit, a knife is provided in said slit on said collar;

a stop block provided with a protrusion and being provided on the bottom of said collar, and being screw connected to said positioning block;

an enveloping ring fitted over said stepped collar being screw connected respectively on said positioning block and said fixing seat, said enveloping ring is provided with a needle hole stub and a slit thereon for receiving said knife in said slit when said needle is aligned with said hole of said collar.

6. The needle extracting and recovering device as claimed in claim 5, wherein a thinner axle is provided in said rotation axle and is tightly abutted on the inner wall of said bottom hollow abutting rod of said cover of said rotating knob.

\* \* \* \* \*